(12) United States Patent
Arsenault et al.

(10) Patent No.: US 10,517,764 B2
(45) Date of Patent: Dec. 31, 2019

(54) PROTECTIVE EYE COVER SYSTEM

(71) Applicants: Mea Madamba Arsenault, Tacoma, WA (US); Sylvia Saiz Sheridan, Lakewood, WA (US)

(72) Inventors: Mea Madamba Arsenault, Tacoma, WA (US); Sylvia Saiz Sheridan, Lakewood, WA (US)

( * ) Notice: Subject to any disclaimer, the term of this patent is extended or adjusted under 35 U.S.C. 154(b) by 0 days.

(21) Appl. No.: 15/374,698

(22) Filed: Dec. 9, 2016

(65) Prior Publication Data
US 2017/0354539 A1    Dec. 14, 2017

Related U.S. Application Data

(60) Provisional application No. 62/347,783, filed on Jun. 9, 2016.

(51) Int. Cl.
*A61F 9/02*      (2006.01)

(52) U.S. Cl.
CPC .............. *A61F 9/026* (2013.01); *A61F 9/025* (2013.01); *A61F 9/029* (2013.01)

(58) Field of Classification Search
CPC .......... A61F 9/025; A61F 9/026; A61F 9/029; A63B 33/02
See application file for complete search history.

(56) References Cited

U.S. PATENT DOCUMENTS

| 5,980,497 | A | * | 11/1999 | Yavitz | A61F 13/124 |
| | | | | | 128/858 |
| 6,098,628 | A | * | 8/2000 | Funk | A61F 13/124 |
| | | | | | 128/859 |
| 7,490,365 | B2 | | 2/2009 | Matsumoto et al. | |
| 2002/0026151 | A1 | | 2/2002 | Miller et al. | |
| 2002/0100481 | A1 | | 8/2002 | Abbasi | |

(Continued)

FOREIGN PATENT DOCUMENTS

| JP | 2017000585 | A | * | 1/2017 |
| WO | 2012094426 | A2 | | 7/2012 |
| WO | 2015028820 | A1 | | 3/2015 |

OTHER PUBLICATIONS

Federal Institute of Industrial Property; PCT/US2017/023572 International Search Report and Written Opinion, dated Aug. 17, 2017, 7 pgs.

*Primary Examiner* — Daniel J Colilla
(74) *Attorney, Agent, or Firm* — Eldredge Law Firm; Richard Eldredge; Beth Felix (57) ABSTRACT

A protective eye cover system comprising a nonporous dome-shaped lens shaped to fit over a human eye cavity and encircle an associated eye. The system also comprises a flexible base ring coupled to the lens, the base ring exhibiting sufficient flexibility to permit close adherence to the eye cavity. An adhesive attached to the base ring promotes a seal of the coupled base ring and lens to surface skin of the eye cavity. The sealing of the coupled base ring and lens to surface skin of the eye cavity prevents liquids from contacting the eye and surrounding area and further protect eyelash extensions from at least one of liquids, steam and heat. The lens is configured with a depth such that an inner surface of the lens does not contact eyelashes and eyelash extensions of a wearer. An anti-fogging agent prevents obstruction of wearer view.

20 Claims, 5 Drawing Sheets

(56) References Cited

U.S. PATENT DOCUMENTS

| | | | |
|---|---|---|---|
| 2005/0193479 A1* | 9/2005 | Atta | A63B 33/002 |
| | | | 2/440 |
| 2008/0148461 A1* | 6/2008 | Guyuron | A61F 9/04 |
| | | | 2/15 |
| 2011/0004969 A1* | 1/2011 | Frohlich | A61F 9/04 |
| | | | 2/15 |
| 2014/0318571 A1 | 10/2014 | Rajkovich et al. | |
| 2016/0067098 A1 | 3/2016 | St. Hilaire | |
| 2016/0250076 A1* | 9/2016 | Geertsen | A61F 9/022 |
| | | | 128/858 |

* cited by examiner

PROTECTIVE EYE COVER SYSTEM

CROSS-REFERENCE TO RELATED APPLICATIONS

The present Utility patent application claims priority benefit of the U.S. provisional application for patent Ser. No. 62/347,783 entitled "EYELASH EXTENSION PROTECTIVE COVERS," filed on 9 Jun. 2016 under 35 U.S.C. 119(e). The contents of this related provisional application are incorporated herein by reference for all purposes to the extent that such subject matter is not inconsistent herewith or limiting hereof.

RELATED CO-PENDING U.S. PATENT APPLICATIONS

Not applicable.

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to beauty products. More particularly, certain embodiments of the invention relates to eye covers that may protect eyelash extensions.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Some individuals may use eyelash extensions or false eyelashes to make lashes appear thicker, longer and fuller. These beauty enhancements may provide time saving conveniences by normally eliminating the need to keep up with a daily routine of curling one's natural lashes and/or applying mascara and the tedious process of removing mascara using mascara cleansers, which often cause eye irritation. Eyelash extensions are typically synthetic, mink or silk strands that may be applied using an eyelash extension adhesive to a person's natural lashes individually; the lashes can be added at a 1:1 ratio, or multiple extension strands can be added to a single natural lash, which is referred to as volume lashes. False eyelashes, also known as strip lashes, are typically full sets of synthetic strands that may be applied above the lash line as a single unit. It is believed that having eyelash extensions may be a commitment in time and resources, as it typically takes 2 to 2.5 hours for a full set application and 1 to 1.5 hours for touch ups and the cost of eyelash extensions may range from $200-$600 or more for a full set. Volume lash extensions in comparison to regular 1:1 extensions are costlier, may take longer to apply and may be more difficult to maintain.

A common method for applying eyelash extensions is to adhere the extensions to the lashes using an adhesive that cures over time. During this curing process a chemical reaction may take place, typically resulting in a harder, tougher, or more stable linkage between the extensions and the lashes. Depending on the type of adhesive being used the curing process may take a few hours or up to three days. The application of faster curing adhesive is frequently more difficult for the eyelash extension practitioner and may tend to give a less than ideal outcome in the appearance of the finished product. Thus practitioners and their clients often prefer to employ slower curing adhesives.

It is believed that lash extension adhesive typically lasts from two to three weeks from application. One may expect that proper care of the extensions may help to prolong the longevity of the eyelash extensions. Properly caring for eyelash extensions may involve limiting contact to water, steam and heat. Water, steam and heat, especially within the first 48 hours following the application of the eyelash extensions, can weaken the extension's adhesive bond to the natural lash, particularly if the adhesive is not yet cured, which thereby can result in the eyelash extensions falling off prematurely. Also, depending on the type of adhesive used, exposure to water, steam or heat before the adhesive cures and even after curing can cause the adhesive to expand, which may make the extensions appear fibrous, which typically equates to the extensions appearing less natural and less attractive. In addition, heat can upset the lash structure causing the curl to go straight and loosen the adhesive bond, which may result in the extensions falling off prematurely. It is also believed that continued protection of the eyelash extensions past 48 hours may help to further prolong the longevity of the extensions.

By way of educational background, an aspect of the related technology generally useful to be aware of is that there are some tools currently available to help protect eyelash extensions in the form of swimming goggles or glasses that surround and cover the eye area. These approaches typically comprise a frame and a bridge piece across the nose that form a relatively large footprint on the face and may include straps that wrap around the head, which may inhibit the user's ability to wash their entire face and their full head of hair. Glasses style approaches may be easily dislodged or completely knocked off, especially in a shower setting. To hold goggles securely to the face, straps around the head and ears may be tight and sometimes uncomfortable. In some instances, goggles may leave the eyes looking puffy or swollen and in some cases can cause bruising. Dermatologist S. Manjula Jegasothy, M.D. in Miami advises that the suction in swimming goggles may also cause laxity of the eye-lids, and the pull from the goggle straps may be considered harsh on ones' eyelids, which may cause capillary breakage, dark circles, deep lines and loose skin. It is believed that swimming goggles may have insufficient depth in the lens to accommodate the length of the extensions, which may bend the lash extensions and affect their shape and longevity. Furthermore, one may expect that adjustments to such goggles or glasses or accidental bumps during use may lead to the seal between the goggles or glasses and the user's skin being broken, which can enable moisture to reach the extensions. In addition, if steam or water penetrates the seal of the goggle or glasses, condensation or fog could be introduced to lenses, which may potentially obstruct the user's view. Moreover, it is believed that neither swimming goggle or glasses style options typically provide protection against heat.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 1A and 1B illustrate exemplary eye covers, in accordance with an embodiment of the present invention.

FIGS. 2A, 2B, 2C, and 2D illustrate the application and removal of an exemplary eye cover to the eye area of a user, in accordance with an embodiment of the present invention.

FIGS. 3A, 3B, and 3C illustrate a pair of exemplary eye covers as applied to the eye areas of a user, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see *Ex parte Mallory,* 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See *Energy Absorption Sys., Inc. v. Roadway Safety Servs., Inc.,* Civ. App. 96-1264, slip op. at 10 (Fed. Cir. Jul. 3, 1997) (unpublished) *Hybridtech v. Monoclonal Antibodies, Inc.,* 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See *Seattle Box Co. v. Industrial Crating & Packing, Inc.,* 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See *In re Frye,* Appeal No. 2009-006013, 94 USPQ2d 1072, 1077, 2010 WL 889747 (B.P.A.I. 2010) Depending on its usage, the word "substantially" can denote either language of approximation or language of magnitude. *Deering Precision*

*Instruments, L.L.C. v. Vector Distribution Sys., Inc.,* 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the specification uses the word "approximately" as a substitute for the word "substantially" (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognized in case law to have the dual ordinary meaning of connoting a term of approximation or a term of magnitude. See *Dana Corp. v. American Axle & Manufacturing, Inc.*, Civ. App. 04-1116, 2004 U.S. App. LEXIS 18265, *13-14 (Fed. Cir. Aug. 27, 2004) (unpublished). The term "substantially" is commonly used by claim drafters to indicate approximation. See *Cordis Corp. v. Medtronic AVE Inc.*, 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also *Deering Precision Instruments, LLC v. Vector Distribution Sys., Inc.*, 347 F.3d 1314, 1322 (Fed. Cir. 2003); *Epcon Gas Sys., Inc. v. Bauer Compressors, Inc.*, 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, *Liquid Dynamics Corp. v. Vaughan Co.*, 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." *In Cordis Corp. v. Medtronic AVE, Inc.*, 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In *Anchor Wall Systems v. Rockwood Retaining Walls, Inc.*, 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see *Deering Precision Instruments, L.L.C. v. Vector Distrib. Sys., Inc.*, 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see *Epcon*, 279 F.3d at 1031 ("The phrase 'substantially constant' denotes language of approximation, while the phrase 'substantially below' signifies language of magnitude, i.e., not insubstantial."). Also, see, e.g., *Epcon Gas Sys., Inc. v. Bauer Compressors, Inc.*, 279 F.3d 1022 (Fed. Cir. 2002) (construing the terms "substantially constant" and "substantially below"); *Zodiac Pool Care, Inc. v. Hoffinger Indus., Inc.*, 206 F.3d 1408 (Fed. Cir. 2000) (construing the term "substantially inward"); *York Prods., Inc. v. Cent. Tractor Farm & Family Ctr.*, 99 F.3d 1568 (Fed. Cir. 1996) (construing the term "substantially the entire height thereof"); *Tex. Instruments Inc. v. Cypress Semiconductor Corp.*, 90 F.3d 1558 (Fed. Cir. 1996) (construing the term "substantially in the common plane"). In conducting their analysis, the court instructed to begin with the ordinary meaning of the claim terms to one of ordinary skill in the art. *Prima Tek*, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see *AK Steel Corp. v. Sollac*, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by *Pall Corp. v. Micron Separations, Inc.*, 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see *Verve LLC v. Crane Cams Inc.*, 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In *Andrew Corp. v. Gabriel Elecs. Inc.*, 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in *Ecolab Inc. v. Envirochem, Inc.*, 264 F.3d 1358, 1367, 60 USPQ2d 1173, 1179 (Fed. Cir. 2001) that "like the term 'about,' the term 'substantially' is a descriptive term commonly used in patent claims to avoid a strict numerical boundary to the specified parameter," see *Ecolab Inc. v. Envirochem Inc.*, 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see *Pall Corp. v. Micron Seps.*, 66 F.3d 1211, 1217, 36 USPQ2d 1225, 1229 (Fed. Cir. 1995); see, e.g., *Andrew Corp. v. Gabriel Elecs. Inc.*, 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see *Ex parte Mallory*, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, *In re Hutchison*, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, are generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of, or interaction with, some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . " Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see *Norian Corp. v Stryker Corp.*, 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

An embodiment of the present invention may provide protection for eyes, eyelashes, and eyelash extensions from liquids, steam and heat effectively and conveniently in a non-cumbersome and easy to apply manner. Some embodiments may be implemented as enclosed, bridgeless, nonporous, waterproof, dome shaped lenses that may be shaped to comfortably adhere to the human eye cavity formed by the orbital bone structure around the eye. These lenses may be intended to cover upper and lower eyelash extensions. Many embodiments may be suitable for use in a variety of environments including, but not limited to, shower settings, saunas, steam rooms, gyms, outdoors, in tanning beds, etc.

Figure 1A:
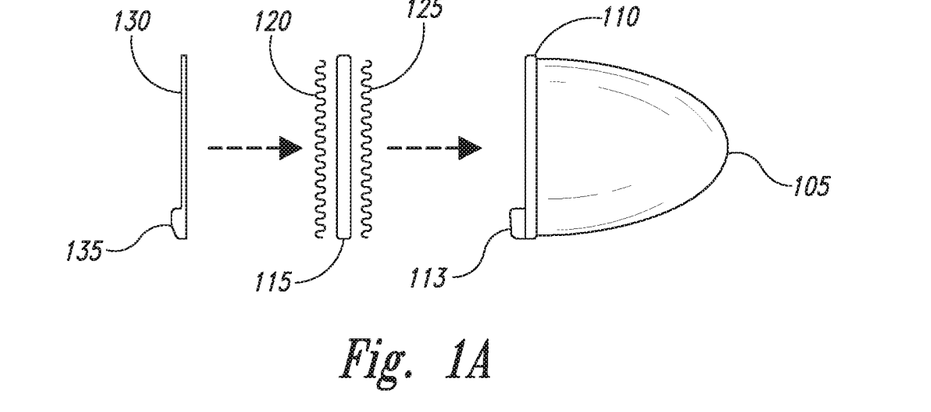
FIG. 1A is an exploded side view the eye covers.
Figure 1B:
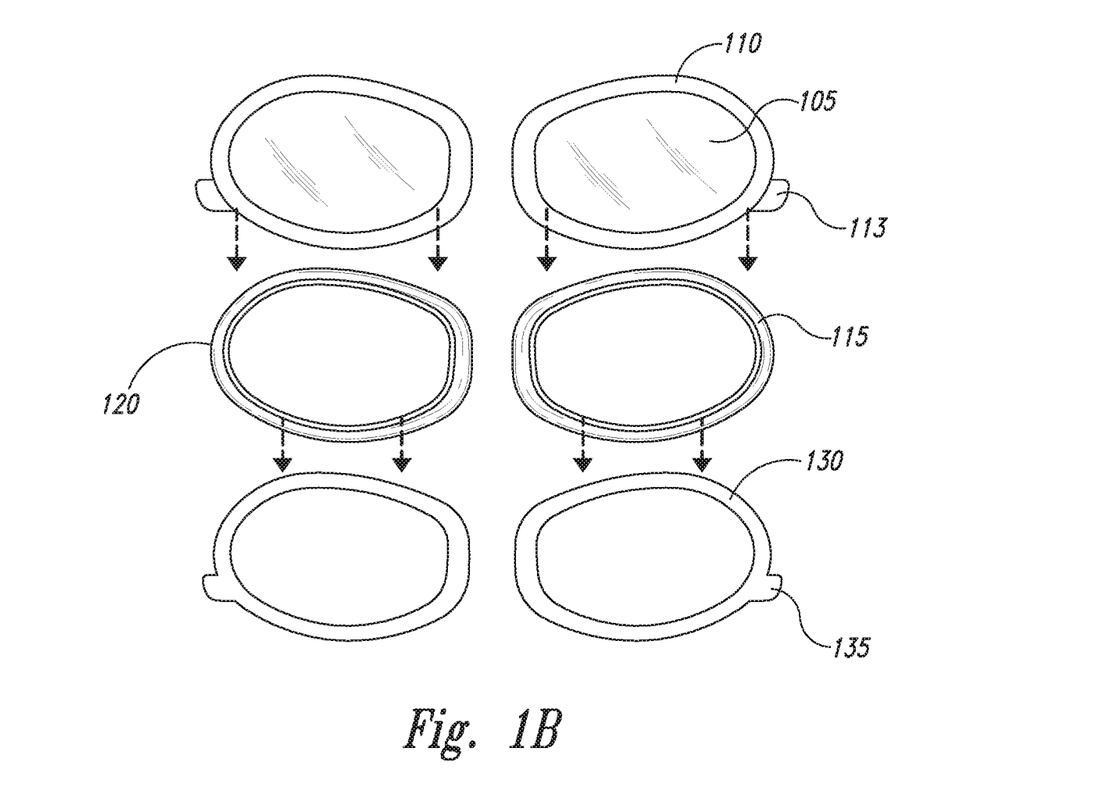
FIG. 1B is a rear exploded view of the eye covers.

FIGS. 1A and 1B illustrate exemplary eye covers, in accordance with an embodiment of the present invention. FIG. 1A is an exploded side view the eye covers, and FIG. 1B is a rear exploded view of the eye covers. In the present embodiment, the eye covers each comprise a dome shaped lens 105 attached to a base ring 110. Base ring 110 may be strategically shaped to conform to a typical eye socket comfortably. In addition, the depth of dome shaped lens 105 may be sufficiently deep to lessen the possibility of extensions being bent as the depth of lens 105 may be designed to accommodate virtually any length of extensions. In some embodiments eye covers may be made available with lenses of multiple different depths to enable a user to choose the depth that is appropriate for them. In the present embodiment, a tab 113 may be attached to base ring 110 which may aid in removal of the eye cover after use. The size, shape and location of tab 113 may vary in some embodiments. Alternate embodiments may be implemented without such a tab. In the present embodiment, dome shaped lens 105 and base ring 110 may be molded as a single piece to allow for simplicity in manufacturing and cost effectiveness. Therefore, lens 105 and base ring 110 may be made of a moldable transparent material such as, but not limited to, polyethylene, polypropylene, polycarbonate, other types of moldable plastics, acrylic materials, fiberglass, glass, clear aluminum, resin, etc. The material used to form lens 105 and base ring 110 may be thin, non-collapsible, and able to keep its form. Furthermore, it may be desirable for the material to be lightweight, so little pressure is felt around the sensitive eye area. Many embodiments of the present invention are not limited to a particular shape, size, depth, density, composition and durability of the lens. Those skilled in the art will readily recognize, in light of and in accordance with the teachings of the present invention, that in some embodiments alternate methods may be used to form the lens structure including, without limitation, vacuum forming, thermoforming, machining, etc., and in such embodiments non-moldable materials may be used. In some alternate embodiments, flexible materials may be used for the lens and base ring. In other alternate embodiments the lens and the base ring may be formed separately and later attached using appropriate means such as, but not limited to, adhesive, welding, press fitting, etc. Depending on the material and manufacturing method chosen to make the eye covers, some embodiments may be intended for one-time usage and then disposal while others may be intended to offer multiple usages per lens.

In the present embodiment, a thin layer of cushioning 115 may be added to base ring 110. It is contemplated that a multiplicity of suitable materials may be used for cushioning 115 including, but not limited to, foam, pliable plastics, silicone, rubber, paper, corrugated fiberboard pads, molded pulp, forms of inflatable air cushioning (e.g., bubble films), etc. One side of cushioning 115 may comprise a thin layer of waterproof and pressure sensitive skin adhesive 120 to connect the cover to the surface skin of the eye socket of a user and comfortably cover eyelashes and eyelash extensions, as illustrated by way of example in FIG. 2C and FIG. 3A. Cushioning 115 and adhesive 120 may work together to offer a comfortable and secure seal between the eye cover and a user's skin to effectively protect extensions from liquids, steam and heat. In the present embodiment, adhesive 120 may be hypoallergenic and/or latex-free to reduce the possibility of an allergic response and of a grade that is suitable and conformable for the delicate eye area. Many embodiments of the present invention are not limited to any specific choice of suitable adhesive substance. The opposite surface of cushioning 115 may comprise an adhesive 125 that may attach cushioning 115 to base ring 110. It is contemplated that alternative embodiments may utilize different assembly methods to connect the cushioning to the base ring such as, but not limited to, press fitting or various welding methods. Other alternate embodiments may be implemented without cushioning in which the skin adhesive is located directly on the base ring of the lens. In embodiments, cushioning 115 may be manually attached to base ring 110.

In the present embodiment, before application, adhesive 120 may be covered by a backing 130 that may be constructed of a thin paper-like material intended to help maintain the stickiness of adhesive 120. A multiplicity of suitable alternate materials may be used to form the backing in some embodiments such as, but not limited to, thin plastic sheets, coated paper, metallic foil, etc. In the present embodiment, the removal of backing 130 from cushioning 115 may be aided by a small tab 135 on backing 130. It is contemplated that the placement of tab 135 may vary in some embodiments. Alternate embodiments may be implemented without a tab. For example, without limitation, one such embodiment may comprise a backing that is slightly larger than the cushioning so the backing extends past the edge of the eye cover. In these embodiments the backing may be configured in shapes that do not follow the outline of the cover such as, but not limited to, solid rectangular shapes, circular shapes, oval rings, etc. In embodiments intended for multiple usages, the backing material may be reapplied to help maintain the stickiness of the adhesive between uses. Some reusable embodiments may be provided with a storage case, which may help to preserve the stickiness of the adhesive and provide protection for the lens. In other reusable embodiments, an option may be to manufacture and provide the lens and base ring portion of the cover separately from the cushioning and/or adhesive portion. In these embodiments the user can add the adhesive portion to the lens portion prior to each use. This may enable the user to purchase replacement adhesive portions when needed while reusing the same lens portion repeatedly.

Figure 2A:
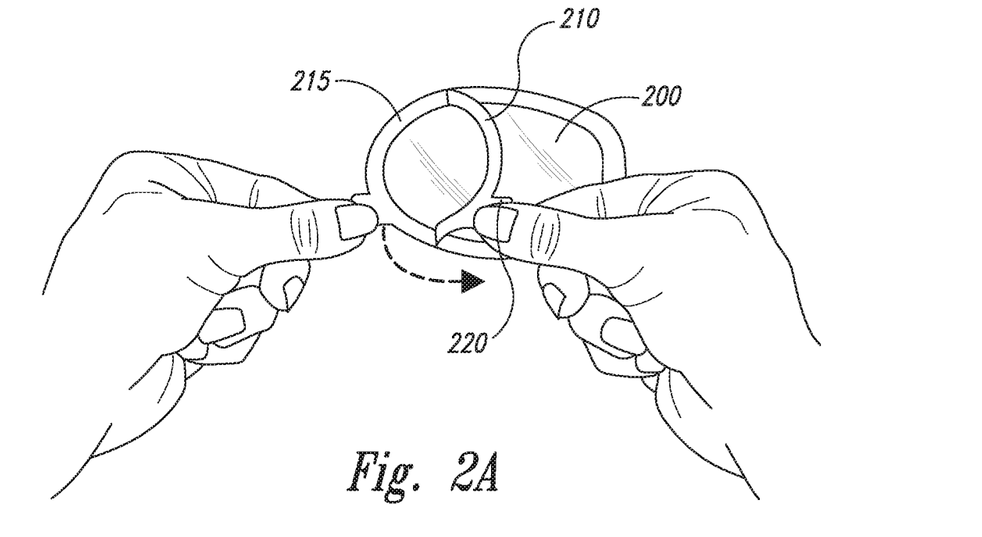
FIG. 2A is a rear view of a backing being removed from the eye cover.
Figure 2B:
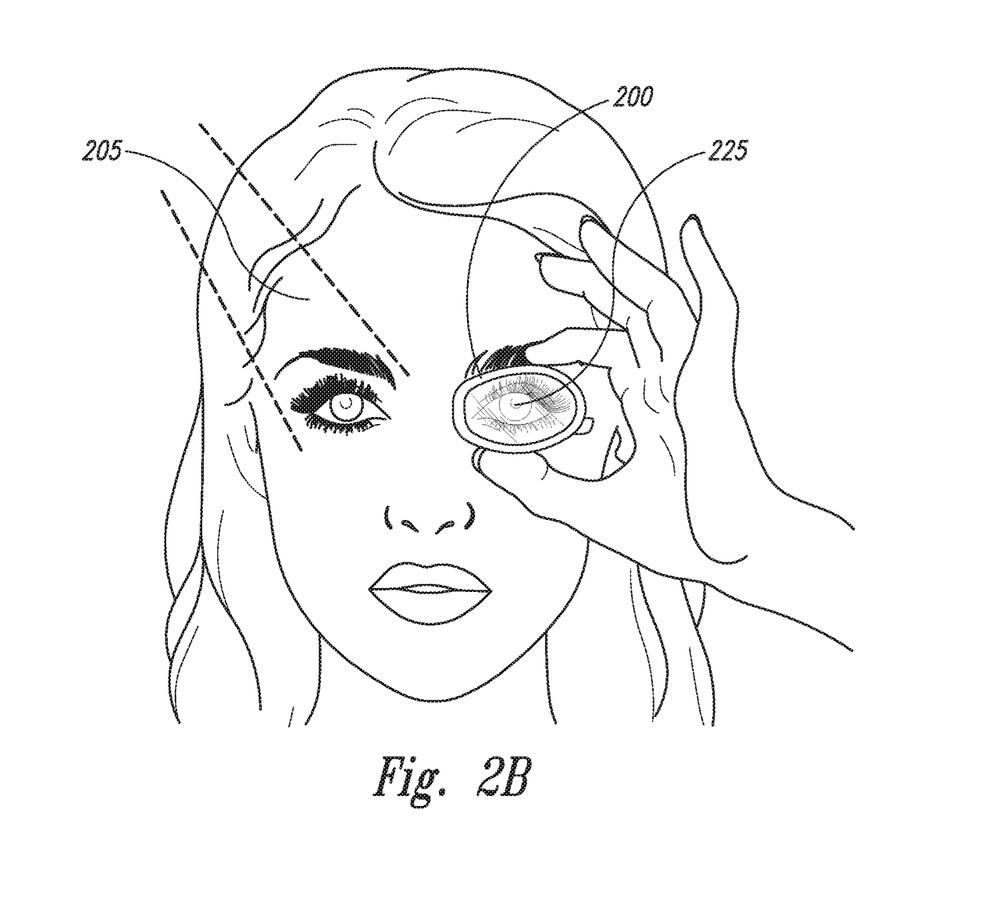
FIG. 2B is a front view of the eye cover being placed over an eye of the user.
Figure 2C:
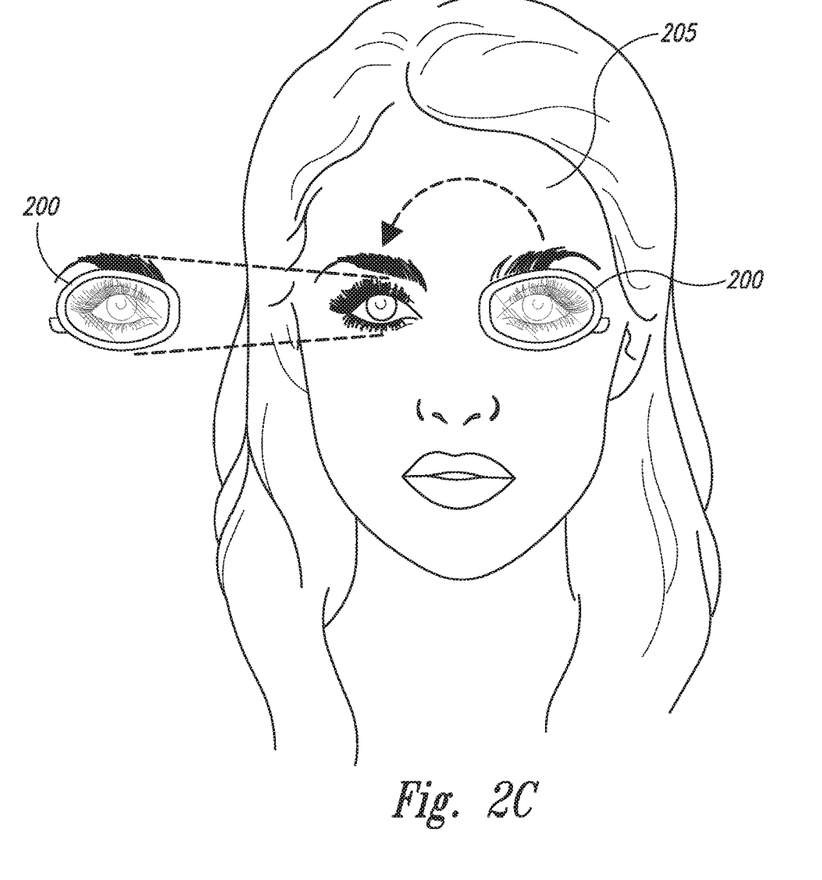
FIG. 2C is a front view of the eye cover in place on the user.
Figure 2D:
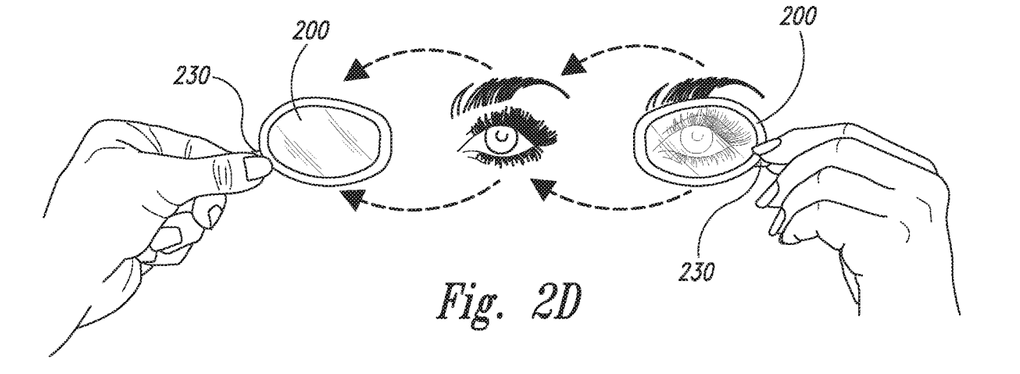
FIG. 2D is a front view of the cover being removed from the eye area.

FIGS. 2A, 2B, 2C, and 2D illustrate the application and removal of an exemplary eye cover 200 to the eye area of a user 205, in accordance with an embodiment of the present invention. FIG. 2A is a rear view of a backing 210 being removed from eye cover 200. FIG. 2B is a front view of cover 200 being placed over an eye 205 of user 205. FIG. 2C is a front view of cover 200 in place on user 205, and FIG. 2D is a front view of cover 200 being removed from the eye area. Referring to FIG. 2A, in the present embodiment, prior to application of cover 200, backing 210 may be removed to expose an adhesive 215. The removal of backing 210 may be aided by the use of a backing tab 220. Referring to FIG. 2B, then cover 200 may be applied around an eye 225 with adhesive 215 in contact with the skin of user 205. User 205 may place cover 200 so that cover 200 comfortably covers both the upper and lower eyelash extensions. Then, cover 200 may be lightly pressed so that adhesive 215 may create a secure seal with the skin around eye 225 that may protect the extensions from liquid, steam and heat. Referring to FIG. 2C, cover 200 is configured to be interchangeable between the left and right eye by simply flipping cover 200 around. This may enable the same mold to be used to manufacture covers for both left and right eyes. In some embodiments covers may be implemented in two separate shapes so that one may be used for a left eye and the other may be used for a right eye. Referring to FIG. 2D, when user 205 is ready to remove cover 200, a cover tab 230 may be used to aid with removal. User 205 may grasp cover tab 230 and peel cover 200 from the skin around the eye area. In embodiments that do not comprise a tab on the base ring, the user may grasp the lens or a portion of the base ring to peel the cover from the eye area.

Figure 3A:
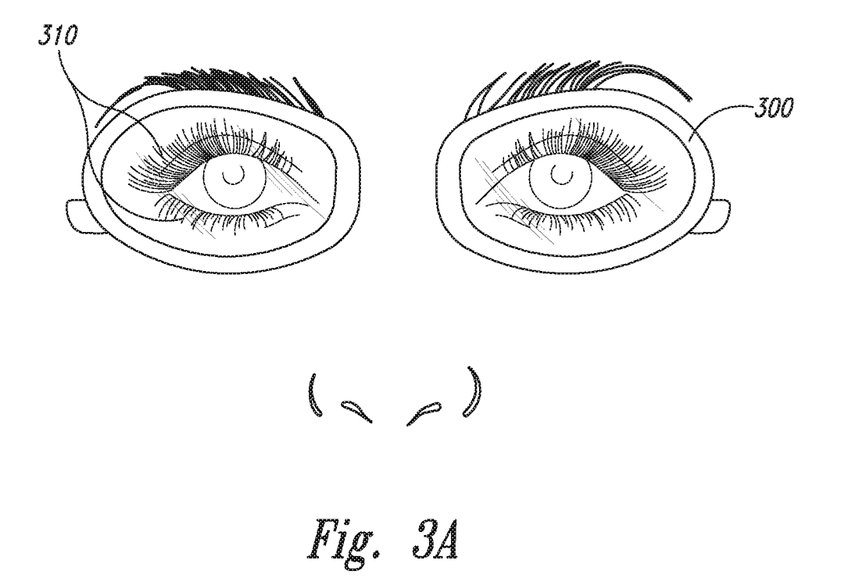
FIG. 3A is a front view.
Figure 3B:
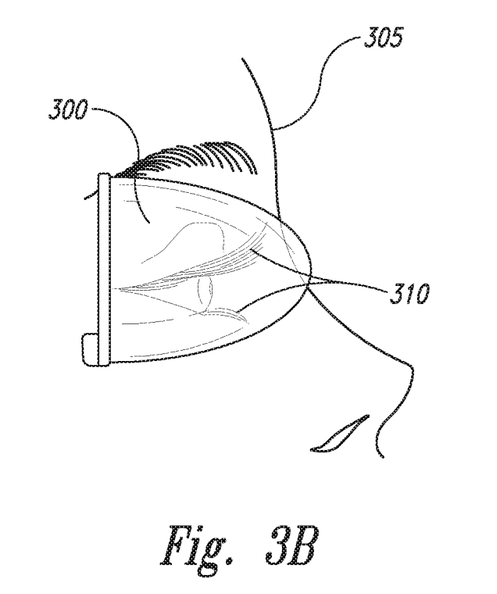
FIG. 3B is a side view.
Figure 3C:
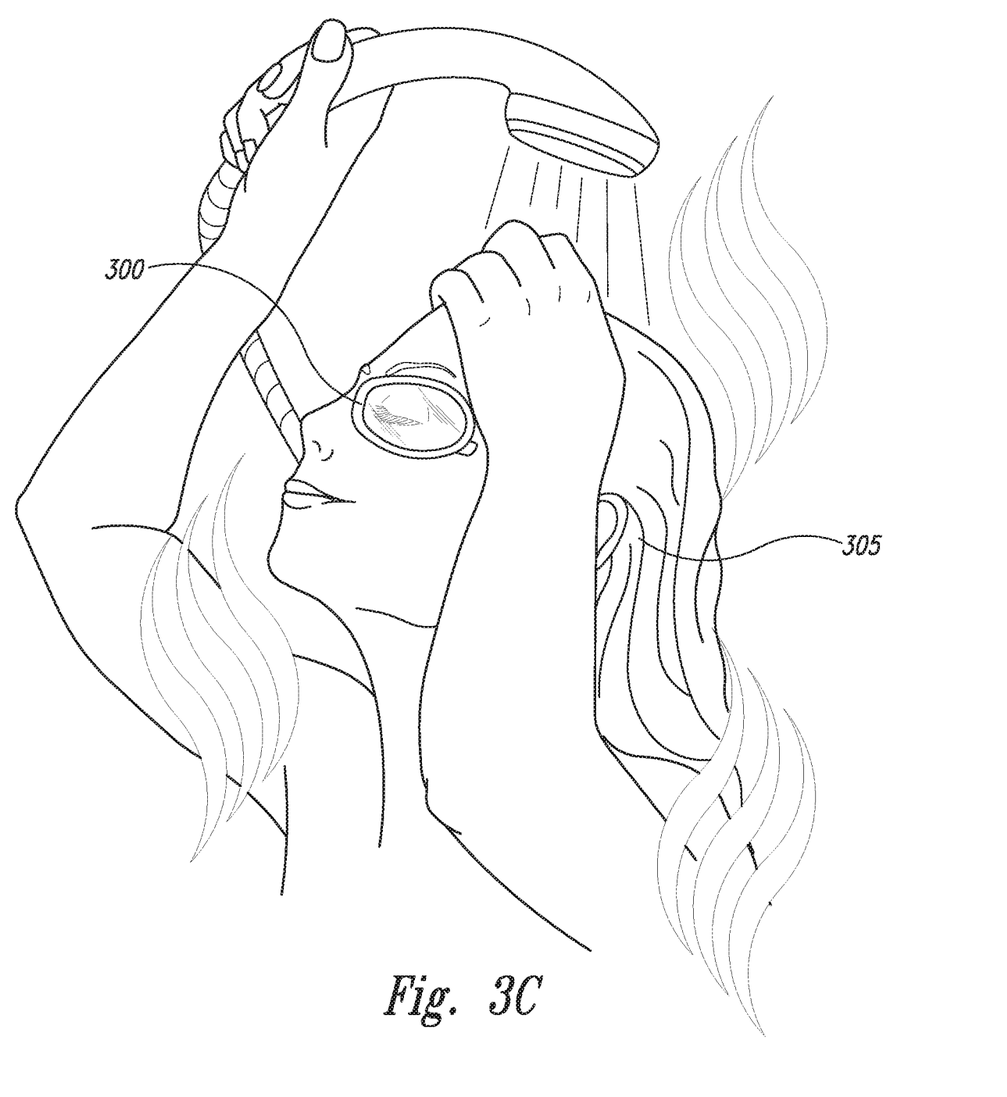
FIG. 3C is a side perspective view of the user using the eye covers while showering.

FIGS. 3A, 3B, and 3C illustrate a pair of exemplary eye covers 300 as applied to the eye areas of a user 305, in accordance with an embodiment of the present invention. FIG. 3A is a front view. FIG. 3B is a side view, and FIG. 3C is a perspective side view of user 305 using eye covers 300 while showering. In the present embodiment, the adhesive in combination with the design of covers 300 to conform comfortably to the orbital bone of user 305 may typically offer a secure bond between covers 300 and the skin of user 305. Referring to FIG. 3B, the depth of the lens of cover 300 may be deep enough to typically ensure that eyelash extensions 310 do not touch the lens, whereby protecting extensions 310 from being bent while still offering protection for eyelash extensions 310. In addition, covers 300 typically have a small footprint, covering only a small portion of the face of user 305. Referring to FIG. 3C, this small footprint along with the absence of a strap that goes around the head and a connecting nose piece may typically allow user 305 to wash their hair and face comfortably and thoroughly even when wearing covers 300. Moreover, the use of an adhesive to hold covers 300 in place may enable user 305 to move portions of their face without breaking the seal and causing a leak. It is believed that covers 300 typically will not cause puffiness, bruising, laxity of the eye-lids, capillary breakage, dark circles, deep lines and loose skin, which may sometimes occur when using current approaches that are secured to the head by straps and strong suction. In the present embodiment the lens portions of covers 300 may comprise an anti-fogging agent that may help ensure that the vision of user 305 is not obscured by the steam and heat in a shower setting. The adhesive seal created by covers 300 is intended to protect extensions 310 from the water of the shower as well as from steam and heat. The lens is nonporous and acts as a barrier from heat, e.g., dry heat emitted from opening a hot oven, or heat from a steam room. The adhesive and/or cushioning may also have waterproofing attributes that may further contribute as a form of barrier/seal not only from water and steam, but also from heat in similar circumstances. The lens material, cushioning and adhesive are not limited in its properties and may also include some form of heat reflective, or heat insulating properties. Thus it is contemplated that covers 300 may also be used effectively in a steam room or sauna. Furthermore, in some applications users may use covers 300 in other types of settings such as, but not limited to, gym settings, swimming in a pool, on the beach, and during other similar outdoor and public activities.

Those skilled in the art will readily recognize, in light of and in accordance with the teachings of the present invention, that some embodiments may be used in a wide variety of different scenarios to protect the eye area, whether a person has eyelash extensions or not. For example, without limitation, some embodiments may be used to protect eyes and extensions during a facial, as often steam is involved. Some embodiments may be used during or after a medical procedure such as, but not limited to, Lasik, or cataract surgery that requires some form of eye protection from water, steam and heat. Some embodiments may house a form of heating element (e.g., encapsulated microwaveable beads, or gels, etc.) to act as a warm compress. Warm compresses assist with treating dry eyes that may help to liquefy the oil that may be stuck within the glands. Additionally, some embodiments may house a cooling element (e.g., enclosed beads, or gels, etc.) put in a freezer, to help reduce eye puffiness, dark circles around the eyes and inflammation caused by allergens by constricting the blood vessels in the skin under the eyes. Some embodiments may also be used to protect the eyes following a cosmetic tattoo procedure, such as, but not limited to, the application of permanent eyeliner. Some embodiments may be used to protect one's eye makeup including, but not limited to, mascara, eyeliner and eyeshadow from water, steam and heat. In some embodiments the lenses may be tinted or opaque as opposed to transparent to obstruct light and allow the user to relax and sleep, for instance, without limitation, during a facial or a massage that may include water, steam, heat, and rubbing oil. In some cases, an opaque cover may be used as a substitute for a traditional eye patch. In some embodiments UV (ultraviolet) and SPF (Sun Protection Factor) protection may be added to the lenses for use in tanning beds, on the beach or poolside which may cause the user to perspire; these embodiments may protect eyelash extensions from perspiration. Antiglare properties and polarization may be added to some embodiments. Eye covers may protect eyelash extensions from perspiration during various different types of activities such as, but not limited to, aerobic exercises, hiking, sports, yard work, etc. Some embodiments may be used in place of swimming goggles when swimming or other types of water activities. Other embodiments may comprise lenses of different colors to protect from computer eye strain. Some embodiments may be used to help prevent eye rubbing or to protect the user and others from eye infections such as, but not limited to, pink eye. Users may employ eye covers according to various embodiments for protection from a wide variety of things including, without limitation, pet allergies, wind, wind-carried debris such as dust, cold, watersports, firearm usage, jobs that require eye protection, paint, dirt, construction particles, chemicals, etc. It is contemplated that embodiments of different sizes can be made for infants and children in need of eye protection, for instance, without limitation, so they do not scratch their eyes.

Another embodiment of the present invention may comprise an enlarged domed lens that may be able to provide protection to eyebrows along with eyelash extensions, as eyebrow extensions are becoming a trend. Similarly, to eyelash extensions, eyebrow extensions also require protection from water, steam and heat, particularly within the first 48 hours from application. Some embodiments may be shaped specifically for the protection of eyebrow extensions separate from eyelash extensions. Such embodiments may differ from eyelash extension covers in shape and density. These embodiments may not need to be transparent as they typically do not cover the eyes of the user. Eyebrow extension covers can also be used after a micro-blading procedure, which is a manual method used to deposit small amounts of ink in the superficial layer of the skin, similar to a semi-permanent tattoo or following a more permanent tattoo cosmetic procedure done on the brows. It is contemplated that other embodiments may be shaped to cover other parts of the body such as, but not limited to, ears, belly buttons, noses, lips, recently pierced or tattooed areas, injured areas where a bandage may be difficult to use, etc. Yet other embodiments may be implemented to be used to protect the eyes of animals and pets for reasons such as, but not limited to, injury or surgery. Additional animal examples for daily use may include an embodiment intended to cover the eyes of horses with a non-see through lens in order to relax them from environment stressors, or a see through lens option to protect their eyes from flies.

It is further contemplated that some embodiments may incorporate additional beauty and relaxation treatments. For example, without limitation, in some embodiments the adhesive could incorporate soothing qualities, so that the covers not only protect eyes, but may also help soothe the areas surrounding the eye. The adhesive could possibly incorporate anti-aging related topical agents as well. In some applications in which a user uses eye covers for purposes other than protecting the lashes, an element can be added within the lens such as, but not limited to, steam, ice or oils to offer varying benefits such as, but not limited to, hydration, reduction of puffiness, growth and strengthening of natural lashes, etc. In some applications oil may be used to help remove the adhesive securing lash extensions when the intention is to remove the extensions by incorporating an appropriate adhesive remover. Users may also seal essential oils in hydrosol form within eye covers for aromatherapy, homeopathic or naturopathic remedies for the eyes.

Another embodiment of the present invention may comprise telescoping lenses that may accommodate eyelash extensions of various different lengths. Telescoping lenses may also be able to collapse to a substantially flat configuration, which may be easier to travel with than domed lenses. This embodiment would most likely be implemented as a reusable version, but is not limited to being reusable.

Those skilled in the art will readily recognize, in light of and in accordance with the teachings of the present invention, that dome shaped lenses similar to those described by way of example in the foregoing may be incorporated into a multiplicity of suitable devices in which a user may wish to accommodate the length of lash extensions including, but not limited to, eye masks to provide protection to the extensions while sleeping, swimming goggles, flying goggles, other types of goggles, cooking glasses and onion/ garlic glasses, gel masks, prescription and non-prescription fashion glasses and sunglasses, reading glasses, lab eyewear, 3D glasses, camera viewfinders, magnifying eye pieces, games that incorporate eye pieces, biometrics security systems that scan the retina, light therapy glasses, meditation glasses, ophthalmological equipment, etc. Moreover, some embodiments of the present invention may be implemented with numerous additional and alternative features such as, but not limited to, various designs on the lenses to add a whimsical or decorative touch, carrying and storage cases, marks or other indicators on the lenses to aid in centering the cover over the eye, means for connecting two covers together, etc.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied.

A first coupled base ring 110 and lens 105 is configured to seal to a first human eye cavity of a wearer separately from and independent of a second coupled base ring 110 and lens 105 configured to seal to a second human eye cavity of the wearer. The two eyes of a wearer may be covered in manners provided herein separate and unrelated to one another.

The seal of the coupled base ring 110 and lens 105 to surface skin of the eye cavity is configured to remain intact upon facial movements of the wearer. The wearer may, for example, laugh, talk, smile or blink his or her eyes and the coupled base ring 110 and lens 105 are configured to remain sealed to the wearer as described herein.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing eye covers that may protect eyelash extensions according to the present invention will be apparent to those skilled in the art. Various aspects of the invention have been described above by way of illustration, and the specific embodiments disclosed are not intended to limit the invention to the particular forms disclosed. The particular implementation of the covers may vary depending upon the particular context or application. By way of example, and not limitation, the covers described in the foregoing were principally directed to covers that protect portions of the body implementations; however, similar techniques may instead be applied to covers that protect items other than body parts such as, but not limited to, a watch or other jewelry, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

What is claimed is:

1. A protective eye cover system, comprising:
    a nonporous dome-shaped lens, said nonporous dome-shaped lens having a shape that is configured to fit over a human eye cavity and encircle an associated eye;
    a flexible base ring, wherein said flexible is engaged with said nonporous dome-shaped lens, wherein said flexible base ring is configured to exhibit sufficient flexibility to be operable for substantial engagement with the eye cavity without a strap or arm that goes around the head or a connecting nose piece,
    a cushioning implement, wherein said cushioning implement is engaged with said flexible base ring, and wherein said cushioning implement is further configured to provide a comfortable seal between said flexible base ring and a surface skin of the eye cavity;
    a first adhesive material applied to said flexible base ring, the first adhesive material promoting a seal of said flexible base ring and said cushioning implement;
    a first tab implement, said first tab implement is engaged with said flexible base ring, wherein said first tab implement is configured to aid in a removal or engagement of said flexible base ring with the eye cavity without holding first adhesive material;
    a second adhesive material, said second adhesive material is applied to at least a portion of said cushioning implement, said second adhesive material is configured to be operable for promoting a seal of said cushioning implement to a surface skin of the eye cavity, in which said second adhesive material comprises at least a hypoallergenic material;
    a backing portion; wherein said backing portion is configured to cover said second adhesive material when not in use, and;
    a second tab implement, said second tab implement is engaged with said backing portion, wherein said second tab implement is configured to aid in a removal or engagement of said backing portion.

2. The system of claim 1, in which said sealing of said cushioning implement to the surface skin of the eye cavity is configured to protect an eyelash extension from at least one of liquids, steam and heat.

3. The system of claim 2, in which said nonporous dome-shaped lens is configured with a depth where an inner surface of the nonporous dome-shaped lens does not contact eyelashes and eyelash extensions of a wearer.

4. The system of claim 3, in which said nonporous dome-shaped lens is configured with a depth that is configured to protect an eyelash extension from bending, in which bending potentially causes damage to and loss of longevity of eyelash extensions.

5. The system of claim 1, in which said adhesive material and said second adhesive material are configured to be at least conformable.

6. The system of claim 1, in which a first flexible base ring that is into engagement with a nonporous dome-shaped lens is configured to be operable for sealing to a first human eye cavity of a wearer separately from and independent of a second flexible base ring into engagement with a nonporous dome-shaped lens configured to seal to a second human eye cavity of the wearer.

7. The system of claim 1, in which said nonporous dome-shaped lens is treated with an anti-fogging agent, wherein said anti-fogging agent is configured to prevent a wearer view from becoming obstructed and further configured to prevent build-up of moisture inside the sealed nonporous dome-shaped lens.

8. The system of claim 1, in which the seal of said flexible base ring and nonporous dome-shaped lens to the surface skin of the eye cavity is configured to be operable for remaining intact upon facial movements of the wearer.

9. A method of applying a protective eye cover, comprising the steps of:
    removing, with the aid of a first tab implement, a protective strip from a proximate outer edge of a first base ring, wherein said first base ring is engaged with a first dome-shaped lens;
    exposing a first adhesive material applied to said outer edge of said first base ring, in which said first base ring comprises a second tab implement that is configured to be operable in adding at least one of, a removal and engagement of said first base ring to a skin surface of a wearer without holding said exposed first adhesive material;
    engaging an inner surface of a cushioning ring to said exposed first adhesive material of said first base ring, wherein said inner surface of said cushioning ring is configured to be operable for engaging said outer edge of said first base ring facing away from said dome-shaped lens;
    exposing a second adhesive material applied to an outer surface of said cushioning ring, in which said second adhesive material comprises at least a hypoallergenic material;

placing, with the aid of said second tab implement, said outer surface of said cushioning ring over a first eye socket of a wearer where a first eye associated with the first eye socket is substantially covered; and applying a pressure to said first base ring with said engaged cushioning ring against a surface skin of the first eye socket, thereby at least in part adhering said first base ring and first dome-shaped lens with the surface skin of the first eye socket.

10. The method of claim 9, wherein an inside surface of said first dome-shaped lens do not make contact with at least one of eyelashes and eyelash extensions of a wearer.

11. The method of claim 9, further comprising the steps of adhering a second base ring and second dome-shaped lens to a second eye of the wearer.

12. The method of claim 9, further comprising the steps of removing said cushioning ring from said base ring.

13. The method of claim 12, in which said second adhesive material further comprises a conformable adhesive that is configured to facilitate adherence of said base ring to a surface skin.

14. The method of claim 9, further comprising the steps of treating said first or second dome-shaped lens with an anti-fogging agent to generally prevent a wearer view from becoming obstructed and to further prevent build-up of moisture inside the sealed dome-shaped lens.

15. The method of claim 9, in which adherence of first or second base ring and first or second dome-shaped lens to the surface skin of the first or second eye is not broken upon facial movements of the wearer.

16. A method of applying a protective eye cover, consisting of:

removing, with the aid of a first tab implement, a protective strip from a proximate outer edge of a base ring, wherein said base ring is configured into engagement with a dome-shaped lens;

exposing a first adhesive material applied to said outer edge of said first ring, in which said base ring comprises a second tab implement that is configured to aid in a removal or engagement of said base ring to a skin surface without holding said exposed first adhesive material;

engaging an inner surface of a cushioning ring to said exposed first adhesive material of said base ring, wherein said inner surface of said cushioning ring being engaged with said base ring facing away from said dome-shaped lens;

exposing a second adhesive material previously applied to an outer surface of said cushioning ring, in which said second adhesive material comprises a hypoallergenic material;

placing, with the aid of said second tab implement, said outer surface of said cushioning ring over an socket of a wearer such that a first eye associated with the first eye socket is substantially covered; and applying a pressure to said base ring with said engaged cushioning ring against a surface skin of the first eye socket, thereby at least in part adhering the coupled base ring and dome-shaped lens with the first eye socket.

17. The method of claim 16, in which said adhering of said coupled base ring and dome-shaped lens to the first eye socket creates a seal preventing external liquids, steam and heat from making contact with the first eye.

18. The method of claim 16, in which an interior surfaces of said dome-shaped lens do not make contact with at least one of eyelashes and eyelash extensions of the wearer.

19. The method of claim 16, in which said adhesive material applied to said outer surface of said cushioning ring is conformable.

20. The method of claim 16, in which said step of exposing the adhesive material previously applied to the outer surface of the cushioning ring comprises removing a protective strip covering the cushioning ring.

* * * * *